(12) United States Patent
Lye et al.

(10) Patent No.: US 7,282,349 B2
(45) Date of Patent: Oct. 16, 2007

(54) SOLVATOCHROMATIC BACTERIAL DETECTION

(75) Inventors: Jason Lye, Atlanta, GA (US); John Gavin MacDonald, Decatur, GA (US); Ning Wei, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 420 days.

(21) Appl. No.: 10/737,574

(22) Filed: Dec. 16, 2003

(65) Prior Publication Data

US 2005/0130253 A1 Jun. 16, 2005

(51) Int. Cl.
*C12Q 1/22* (2006.01)

(52) U.S. Cl. .................. 435/31; 8/400; 436/1
(58) Field of Classification Search .............. 435/31; 8/400; 436/1
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,705,032 A * | 12/1972 | Honjo et al. .................. | 430/91 |
| 3,802,817 A | 4/1974 | Matsuki et al. | |
| 3,849,241 A | 11/1974 | Butin et al. | |
| 4,100,324 A | 7/1978 | Anderson et al. | |
| 4,310,928 A | 1/1982 | Joung | |
| 4,340,395 A * | 7/1982 | Magers et al. ................. | 436/66 |
| 4,340,563 A | 7/1982 | Appel et al. | |
| 4,375,448 A | 3/1983 | Appel et al. | |
| 4,494,278 A | 1/1985 | Kroyer et al. | |
| 4,511,488 A | 4/1985 | Matta | |
| 4,556,636 A | 12/1985 | Belly et al. | |
| 4,640,810 A | 2/1987 | Laursen et al. | |
| 4,677,076 A * | 6/1987 | Langhals ..................... | 436/40 |
| 4,775,582 A | 10/1988 | Abba et al. | |
| 4,780,422 A | 10/1988 | Mitani et al. | |
| 4,818,464 A | 4/1989 | Lau | |
| 4,833,003 A | 5/1989 | Win et al. | |
| 4,853,281 A | 8/1989 | Win et al. | |
| 5,036,000 A | 7/1991 | Palmer et al. | |
| 5,112,900 A | 5/1992 | Buddenhagen et al. | |
| 5,407,715 A | 4/1995 | Buddenhagen et al. | |
| 5,464,739 A | 11/1995 | Johnson et al. | |
| 5,468,469 A | 11/1995 | Aszalos et al. | |
| 5,527,171 A | 6/1996 | Soerensen | |
| 5,534,416 A | 7/1996 | Millard et al. | |
| 5,742,943 A | 4/1998 | Chen | |
| 5,744,321 A | 4/1998 | Harewood | |
| 5,792,531 A | 8/1998 | Littleton et al. | |
| 5,900,452 A | 5/1999 | Plamthottam | |
| 6,090,541 A | 7/2000 | Wicks et al. | |
| 6,168,655 B1 * | 1/2001 | Nohr et al. ................. | 106/31.58 |
| 6,288,159 B1 | 9/2001 | Plamthottam | |
| 6,306,514 B1 | 10/2001 | Weikel et al. | |
| 6,362,006 B1 | 3/2002 | Potyrailo et al. | |
| 6,368,558 B1 * | 4/2002 | Suslick et al. ............... | 422/55 |
| 6,383,815 B1 * | 5/2002 | Potyrailo ..................... | 436/2 |
| 6,524,846 B1 | 2/2003 | Robinson, Jr. | |
| 2003/0119202 A1 | 6/2003 | Kaylor et al. | |
| 2003/0143112 A1 | 7/2003 | Suslick et al. | |
| 2003/0198573 A1 * | 10/2003 | Forood et al. ........... | 422/82.08 |
| 2005/0130253 A1 | 6/2005 | Lye et al. | |
| 2006/0134613 A1 | 6/2006 | Martin et al. | |
| 2006/0134728 A1 | 6/2006 | MacDonald et al. | |

FOREIGN PATENT DOCUMENTS

| | | |
|---|---|---|
| EP | 0517050 A2 * | 12/1992 |
| EP | 0 846 767 A | 6/1998 |
| GB | 1107790 | 3/1968 |
| GB | 2178847 A | 2/1987 |
| WO | WO 9730351 A1 | 8/1997 |
| WO | WO 0233413 A1 | 4/2002 |
| WO | WO 02103356 A1 | 12/2002 |
| WO | WO 2005/016230 A | 2/2005 |
| WO | WO 2005/059162 A | 6/2005 |

OTHER PUBLICATIONS

Zachariasse KA et al (1981) Investigation of micelles, microemulsions, and phospholipid bilayers with the pyridinium-N-phenobetaine ET(30), a polarity probe for aqueous interfaces. J Phys Chem, vol. 85, pp. 2676-2683.*

Griffiths, J., *Colour and Constitution of Organic Molecules*, Academic Press, 1976, pp. 16-81; pp. 146-161.

Levine, B.F. et al., "Solvent dependent hyperpolarizability of a mercocyanine dye", *The Journal of Chemical Physics*, vol. 68, No. 11, Jun. 1978, pp. 5042-5045.

Lehmann, F. et al., "Synthesis and structure-property relationships of amphiphilic acidochromic hydroxystilbazolium dyes", *Sensors and Actuators B Chemical*, vol. B39, 1997, pp. 229-234.

(Continued)

*Primary Examiner*—Jon Weber
*Assistant Examiner*—Clark D. Petersen
(74) *Attorney, Agent, or Firm*—James B. Robinson

(57) ABSTRACT

Solvatochromic dyes are used herein to indicate the presence of bacteria by incorporating them into various substrates such as films, woven and nonwoven fabrics, paper towels, coform and airlaid materials and bonded carded webs. These dyes change color in response to a change in polarity of the environment. Since water is a polar solvent and most bacteria are made from non-polar substances, the presence of bacteria changes the polarity of the environment, triggering a change visible by the unaided eye. A lateral flow device incorporating solvatochromic dyes and a method of detecting bacteria are also included.

20 Claims, 1 Drawing Sheet

OTHER PUBLICATIONS

Grummt, UW. et al., "Second order hyperpolarizability of hydroxystilbazolium salts and their betaines—relationship to chemical structure", *Journal of Materials Chemistry*, vol. 9, No. 7, 1999, pp. 1419-1424.

Zachariasse, K.A. et al., "Investigation of Micelles, Microemulsions, and Phospholipid Bilayers with the Pyridlinium N-Phenolbetaine $E_T(30)$, a Polarity Probe for Aqueous Interfaces", *The Journal of Physical Chemistry*, vol. 85, No. 18, Sep. 1981, pp. 2676-2683.

Plieninger, P. et al., "A $^1$H-NMR Investigation Concerning the Insertion of Pyridinium N-Phenoxide Betaines into Micelles", *Justus Liebigs Ann. Chem.*, Jan. 1983, pp. 860-875.

Greenspan, P. et al., "Nile Red: A Selective Fluorescent Stain for Intracellular Lipid Droplets", *The Journal of Cell Biology*, vol. 100, Mar. 1985, pp. 965-973.

Abstract of Japanese Patent No. 11083849 with XP-002327939, Mar. 26, 1999.

Search Report and Written Opinion for PCT/US2004/042461, Jul. 8, 2005.

Abstract of Article—A'H NMR Investigation Concerning the Insertion of Pyridinium N-Phenoxide Betaines into Micelles, Plieninger et al., Liebigs Ann. Chem. 1983, pp. 860-875.

Article—Second Order Hyperpolarizability of Hydroxystilbazolium Salts and Their Betaines—Relationship to Chemical Structure, Grummit et al., J. Mater. Chem., vol. 9, 1999, pp. 1419-1424.

Article—Potential Antitumor Phenoxazines, Motohashi et al., Medicinal Research REviews, vol. 11, No. 3, May 1991, pp. 239-294.

Article—Rapid Diagnosis of Adenoviral Keratoconjunctivitis by a Fully Automated Molecular Assay, Koidl et al., Ophthalmology, vol. 112, No. 9, Sep. 2005, pp. 1521.e1-1521.e8.

Article—Simplifying Collection of Corneal Specimens in Cases of Suspected Bacterial Keratitis, Kaye et al., Journal of Clinical Microbiology, vol. 41, No. 7, Jul. 2003, pp. 3192-3197.

Article—Development and Use of Nested Polymerase Chain Reaction (PCR) for the Detection of Adenovirus from Conjunctivitis Specimens, Dalapathy, et al., Journal of Clinical Virology 11, 1998, pp. 77-84.

Article—Chloramphenicol Treatment for Acute infective Conjunctivitis in Children in Primary Care: A Randomised Double-Blind Placebo-Controlled Trial, Rose et al., The Lancet. vol. 366, Jul. 2, 2005, pp. 37-43.

Standard Practice for Obtaining Spectrometric Data for Object-Color Evaluation, ASTM International, E-1164, 2002, pp. 1-8.

Paints and Varnishes—Colorimetry—Part 1: Principles, International Standard ISO 7724/1-1984 (E), Oct. 1, 1984.

Methods of Colour Measurement—Reflecting and Transmitting Objects, Japanese Industrial Standard, JIS Z 8722-2000 (E).

Colorimetry, 2nd Edition, International Commission on Illumination, No. 15.2, 1986.

Article—Ocular Virulence of Capsule-Deficient Streptococcus Pneumoniae in a Rabbit Keratitis Model. Reed et al., Investigative Ophthalmology & Visual Science, Feb. 2005, vol. 46, No. 2, pp. 604-608.

Abstract of Detection of Adenovirus DNA in Clinical Samples by SYBR Green Real-Time Polymerase Chain Reaction Assay, Watanabe et al., Jun. 2005.

Abstract of Antimicrobial Resistance Among Clinical Isolates of Haemophilus Influenzae in Northern Italy. Vollaborative Study on Pediatric Infectious Diseases, Garlaschi, et al., Jan. 1993.

Article—The Change in Research for the Therapy of Tumors, Sedlacek et al., Chimia, vol. 45, No. 10, Oct. 1991, pp. 311-316.

Chapters 6 and 9-11 from book entitled Photodynamic Action and Diseases Caused by Light by Harold Francis Blum, American Chemical Society Series of Scientific and Technologic Monographics, 1941.

Article—Nile Red: A Selective Fluorescent Stain for Intracellular Lipid Droplets, Greenspan et al., The Journal of Cell Biology, vol. 100, Mar. 1985, pp. 965-973.

Article—*Pyridinium N-phenolate betaine dyes as empirical indicators of solvent polarity: Some new findings*, Reichardt, Pure Appl. Chem., vol. 76, No. 10, 2004, pp. 1903-1919.

Pocket Guide to Digital Printing, Frank Cost, Delmar Publishers, Albany, NY, ISBN 0-8273-7592-1, pp. 144-145, 1997.

Search Report and Written Opinion for PCT/US2005/038415, Jul. 27, 2006.

\* cited by examiner

SOLVATOCHROMATIC BACTERIAL DETECTION

BACKGROUND OF THE INVENTION

The invention concerns processes and products for the detection of bacteria.

Bacterial contamination of water supplies is a major problem in many parts of the world, developing as well as developed. Recent bacterial contamination outbreaks in various locations in the United States alone have resulted in the death of children and senior citizens and sickening of others. Bacterial contamination of water supplies in the third world is responsible for the death of tens of thousands of people each year.

Water filters are commonly used to remove water impurities and to provide cleaner, more aesthetically pleasing drinking water. They are, however, expensive, bulky, difficult to install and replace. They can harbor harmful organisms, are inconvenient, and do not claim to remove or kill 100 percent of all pathogens.

The more prudent course when the bacterial content of water is unknown is to disinfect it by either boiling or through the use of iodine-based disinfectants. Boiling requires substantial energy, of course, and can lead to the degradation of the environment as trees are cut down for fuel; the practice in many third world countries where water supplies are most vulnerable. Iodine-based disinfectants, however, are not readily available everywhere. It is also well known that some of the iodine-based disinfectant systems currently available leave a distinctively bad taste in the mouth. Potentially adverse medical effects can also arise from the consumption of iodine for individuals having particular medical problems.

Bacterial contamination of food is also a major problem throughout the world. *Salmonella, E. coli* and other food borne bacteria cause untold numbers of illness each year. Acute symptoms include nausea, vomiting, abdominal cramps, diarrhea, fever and headache. Chronic consequences may follow after the onset of acute symptoms. Clearly, having the ability to easily detect the presence of bacteria in food would be of great benefit.

Certain infectious diseases like, for example, chlamydia, are bacterial in nature. The rapid detection of such infections could result in more appropriate and/or more rapid treatment and relief for the sufferers of such maladies.

In our everyday life we are unknowingly exposed to microbial contaminated surfaces which can lead to illness. Studies have shown specific bacterial contaminated "hot spots" to include; public telephone, door handles, toys in doctors waiting rooms and child care facilities, hot air dryers to dry hands, towels and sponges used in the kitchen, the hands of hospital staff during routine patient care and cross contamination from food preparation surfaces and knives where raw meats and vegetables are mixed.

Lastly, rapid detection of other bacteria, like those in biological warfare agents, would allow a more rapid response to protect those exposed. Existing detection systems for such agents are slow, bulky, expensive and prone to error.

It is clear that there exists a need for a process and product which allows for the rapid detection of whether bacteria are present.

SUMMARY OF THE INVENTION

In response to the foregoing difficulties encountered by those of skill in the art, we have discovered that solvatochromic dyes may be used to detect bacteria and more specifically that the addition of solvatochromic dyes to various substrates may be used to indicate the presence of bacteria. These dyes provide a color change that is visible to the unaided eye in response to a change in polarity of their environment. The dye may be coated onto a wipe, for example, using a number of different methods, dried, and then the wipe rubbed against a surface suspected of harboring bacteria. The wipe will change color if bacteria are present.

Examples of solvatochromic dyes include Reichart's dye, merocyanine dyes, 4-[2-N-substituted-1,4-hydropyridin-4-ylidine)ethylidene]cyclohexa-2,5-dien-1-one, red pyrazolone dyes, azomethine dyes, indoaniline dyes, diazamerocyanine dyes, indigoid dyes, as exemplified by indigo, and others as well as mixtures thereof.

Hydroxypropyl-beta-cyclodextrin has been found to be effective in enhancing the brightness of the solvatochromic dye color after it is has been coated onto a paper towel or similar wipe material. While not wishing to be bound by theory, we believe that the color of the dyes is improved by the addition of a cyclodextrin derivative by inhibiting the crystallization of the dye. Other chemicals may be added to a wipe to help prevent false positive readings due to the presence of bleach, which has been found to interfere with the dye.

Lateral flow devices incorporating solvatochromic dyes are also included within the teachings of the invention. These devices have a membrane having detection and control zones, where the detection zone changes color in response to the presence of bacteria and the control zone remains the original dye color to indicate that the assay is functioning properly.

Lastly, a method of detecting bacteria through the use of a wipe having thereon a solvatochromic dye is included herein.

DETAILED DESCRIPTION OF THE INVENTION

Figure 1:
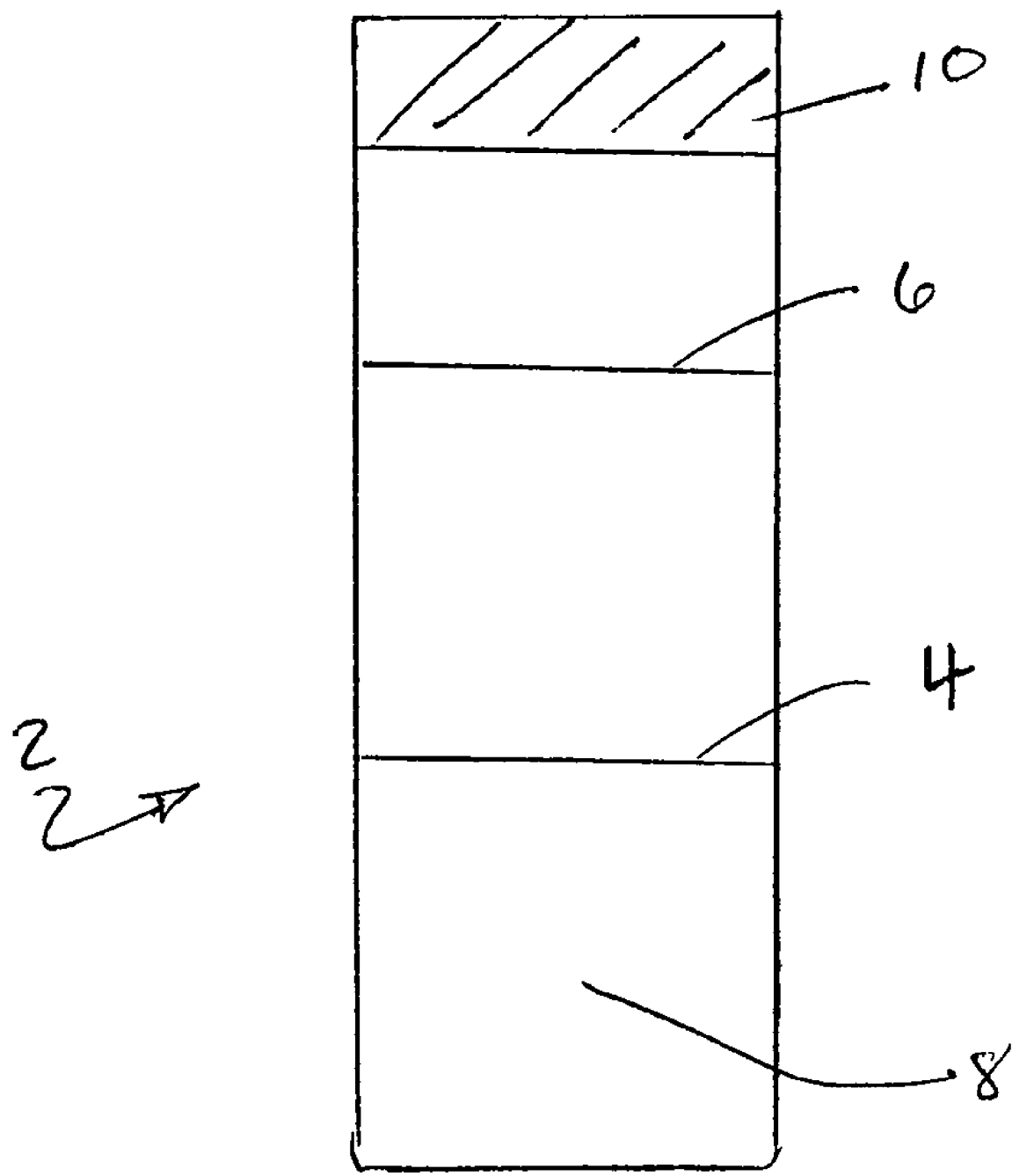
FIG. 1 is a drawing of a lateral flow device suitable for use in the practice of the invention.

The present invention involves the solvatochromatic detection of bacteria.

Solvatochromatism is, most generally, the changing of the perceived color of a dye in response to a change in the solvent in which the dye is dissolved. This change is usually in the polarity of the environment of the dye. A dye may be blue in color in a polar environment such as water, for example, but may be yellow or red in a non-polar environment such as lipids. The colors produced by such "solvatochromic dyes" depend on the molecular polarity difference between the ground and excited state of the dye as discussed more fully below.

More basically, "color" is a type of sensation that arises when the human eye physiology detects the presence or absence of light of various wavelengths reflected or emitted from objects in the visual field. Light entering the eye is subjected to a spectral analysis by three types of retinal cone cells that are sensitive to specific regions of the visible spectrum. Stimuli from these cells are in turn processed by retinal neurons, optic nerve neurons and the visual cortex such that a sensation of color is experienced.

While several mechanisms exist to impart color (for instance, absorption, emission, fluorescence, phosphorescence, refraction, diffraction, etc.) the solvatochromic focus is limited to absorptive color. In other words, this invention relates to dyes that owe their color to absorbing certain frequencies of light.

Because of the way in which the human eye functions, the color perceived is usually the complement of the color associated with the wavelength of light being absorbed by the object. An object that appears to be red in color when viewed in white light, for example, is in fact selectively absorbing bluish light in the range of 490 to 500 nm wavelength. Similarly, an object that appears yellow in white light is in fact absorbing blue light in the range of 435 to 480 nm.

Absorption of visible light by molecules is associated with electronic transitions within the molecule and results in the generation of an excited state. The energy difference between the ground state of the molecule and the relevant excited state determines the wavelength of the light absorbed according to the Planck relationship:

$$E = h\nu$$

Where E=energy, h=Planck's constant, ν is the frequency of the photon of light absorbed, and is related to wavelength λ and the speed of light c by:

$$\nu = c/\lambda$$

A state diagram may be used to depict electronic transitions graphically:

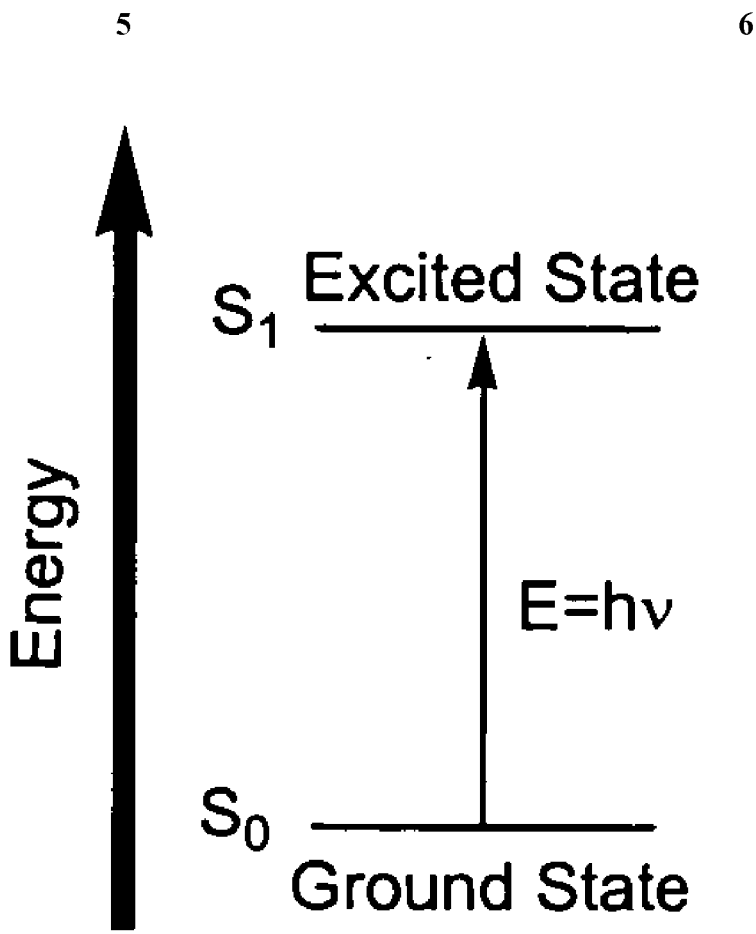

Clearly, the energy of the photon absorbed is inversely proportional to the wavelength of the photon. Thus, photons of blue light (435-480 nm) have higher energy than yellow light (580-595 nm). The color of a dye in solution or on an object when viewed under white light, therefore, is determined by the transition energy between the ground state of the dye molecule and the first allowed excited state.

Environmental factors, i.e., the molecular environment of the dye, may interact with the electronic states of the molecule. If the ground state of the dye is very polar, for example, the ground state of the dye will be stabilized, or reduced in energy, when in a polar environment. Similarly, if the excited state of the dye is polar, the excited state will be stabilized in polar solvents, and destabilized (or increased in energy) when the dye is in non-polar environments.

The difference between the polarity of the ground and excited states of dyes is usually small, and so the net change in transition energy in differing environments is also small. Solvatochromic dyes are unusual in that the polarity of the lowest energy allowed excited state is very different from that of the ground state. In other words, significant changes in atomic electron densities are associated with electronic transitions which lead to large changes in the transition energy for the molecule in different environments.

Case 1

A dye with a ground state that is more polar than the excited state results in, when dissolved in a polar environment, the ground state being stabilized, and the excited state being destabilized, increasing the transition energy, thereby causing a hypsochromic shift (a shift of the maximum absorption wavelength to shorter wavelengths, or a "red shift" in color). This phenomenon may be depicted using state diagrams:

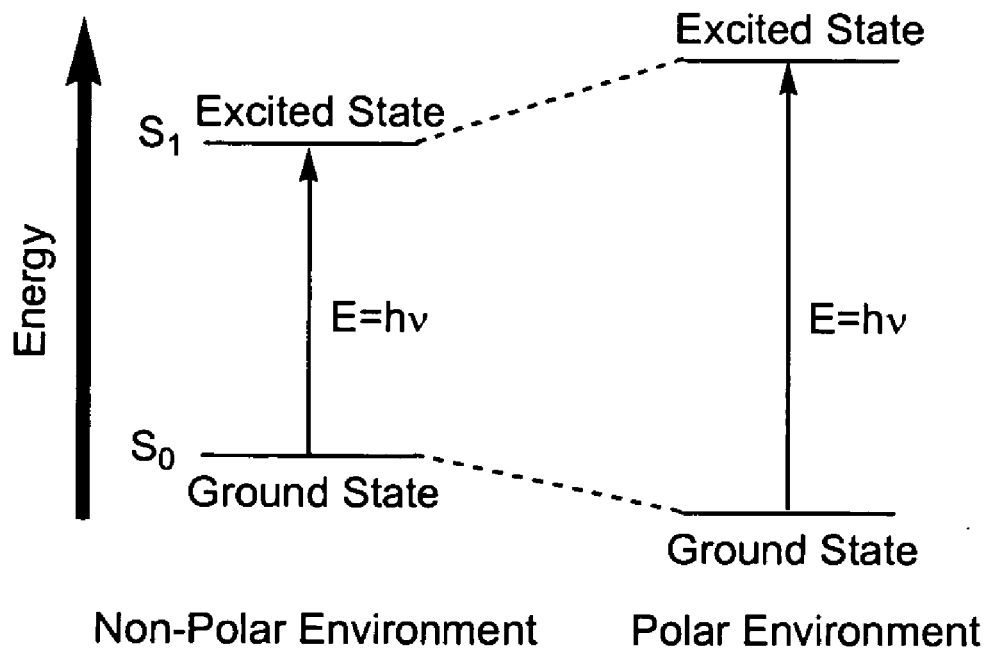

An example of a dye that has a ground state more polar than the excited state is the merocyanine dye as shown below. The charge separated left hand canonical is a major contributor to the ground state whereas the right hand canonical is a major contributor to the first excited state.

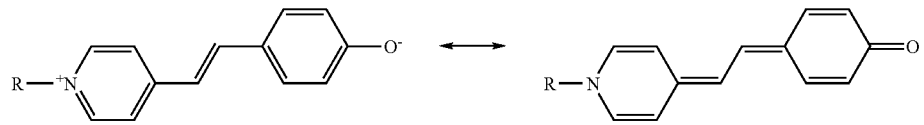

Case 2

The case of a dye with a ground state that is less polar than the excited state results in, when dissolved in a polar environment, the ground state being destabilized, and the excited state being stabilized, decreasing the transition energy, thereby causing a bathochromic shift (a shift of the maximum absorption wavelength to longer wavelengths, or a "blue shift" in color). This phenomenon may be depicted using state diagrams:

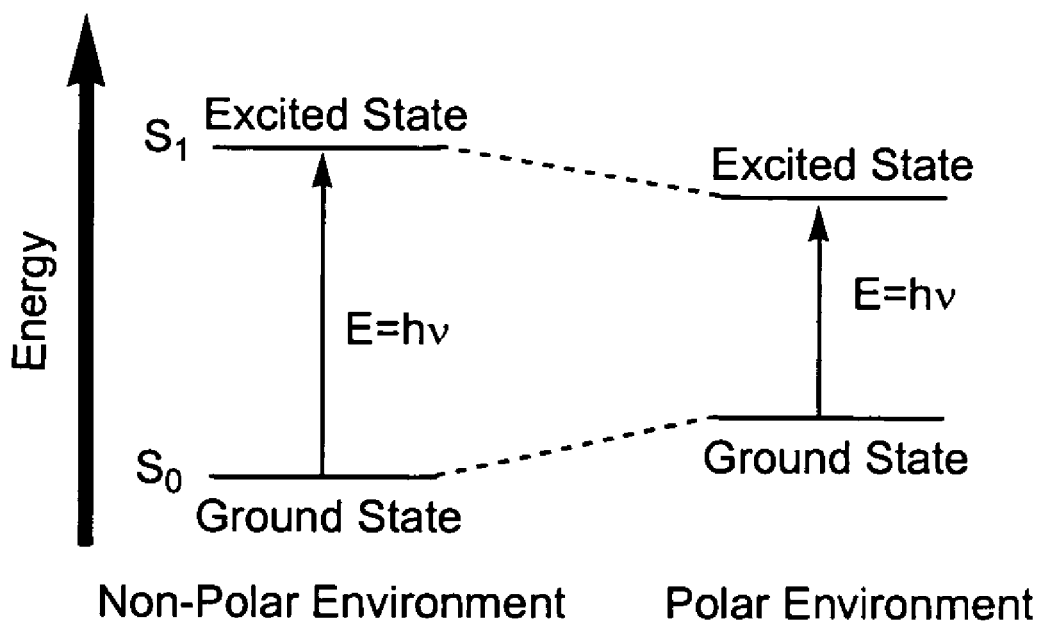

Indigo, as shown below, is an example of a dye that has a ground state that is significantly less polar than the excited state. The left hand canonical form is a major contributor to the ground state of the dye, whereas the right hand canonical is a major contributor to the excited state.

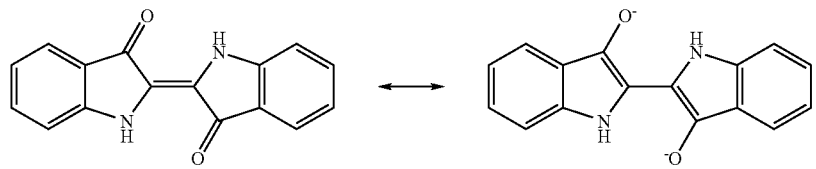

Thus the color of solvatochromic dyes depends upon the immediate polarity environment of the dye because solvent polarity plays a significant role in determining state energy levels. Hydrogen bonding effects and other environmental factors also contribute to solvent polarity levels but to a lesser degree.

The polarity environment has been found by the inventors to be dependent upon the presence or absence of bacteria. Water is a polar solvent. Bacteria have a bi-lipid cell membrane that has a less polar interior. The presence of bacteria, therefore, results in a change in the polarity environment of the solvent that can be detected by the proper solvatochromic dye in the appropriate amount. A suitable dye should have at least a 100 nm differential in absorption wavelength between water and ethanol (a non-polar solvent).

Bacteria that may effect the polarity of an aqueous solution include gram negative bacteria like *Actinomyces, Bacillus, Bifodobacterium, Cellulomonas, Clostridium, Corynebacterium, Micrococcus, Mycobacterium, Nocardia, Staphylococcus, Streptococcus* and *Streptomyces* and gram positive bacteria like *Acetobacter, Agrobacterium, Alcaligenes, Bordetella, Brucella, Campylobacter, Caulobacter, Enterobacter, Erwinia, Escherichia, Helicobacterium, Legionella, nesseria, Nitrobact, Pasteurelia, Pseudomas, Rhizobium, Rickettsia, Salmonella, Shigella, Thiobacilus, Veiellonealla, Vibrio, Xanthomonas* and *Yersinia*.

Gram negative bacteria have cell walls that are mainly lipopolysaccharide. Additionally there is present phospholipid, protein, lipoprotein and a small amount of peptidoglycan. The lipopolysaccharide consists of a core region to which are attached repeating units of polysaccharide moieties. A component of the cell wall of most Gram-negative bacteria is associated with endotoxic activity, with which are associated the pyrogenic effects of Gram-negative infections. On the side-chains are carried the bases for the somatic antigen specificity of these organisms. The chemical composition of these side chains both with respect to components as well as arrangement of the different sugars determines the nature of the somatic or O antigen determinants, which are such an important means of serologically classifying many Gram-negative species. In many cases it has been shown that the reason for certain organisms belonging to quite different species, giving strong serological cross-reactivity, is due their having chemically similar carbohydrate moieties as part of their lipopolysaccharide side chains, which generally have about 30 repeating units.

Gram positive bacteria are characterized by having as part of their cell wall structure peptidoglycan as well as polysaccharides and/or teichoic acids. The peptidoglycans, which are sometimes also called murein, are heteropolymers of glycan strands which are cross-linked through short peptides.

The basis of the murein of chains of alternating residues of N-acetylglucosamine and N-acetyl muramic acid which are Beta-1,4-linked. The muramic acid is a unique substance associated with bacterial cell walls. These chains are cross-linked by short polypetide chains consisting of both L- and D-aminoacids. While in Gram-negative bacteria the peptidoglycan is simple in structure and comparatively uniform throughout most genera, in Gram-positive bacteria there is a very big variation in structure and composition. In general the peptidoglycan is multilayered. There have also been recorded some minor variations in composition in some groups. Thus, in *Mycobacterium* and *Nocardia* the N-acetyl moiety of the muramic acid is replaced by the oxydised form N-glycolyl. The amino acid composition of the both the cross-linking as well the stem polypeptides can vary extensively with different groups. These differences form the basis for the taxonomy of these organisms.

Suitable dyes for the practice of this inventions include those discussed above as well as Reichart's dye, merocyanine dyes, 4-[2-N-substituted-1,4-hydropyridin-4-ylidine) ethylidene]cyclohexa-2,5-dien-1-one, red pyrazolone dyes, azomethine dyes, indoaniline dyes, diazamerocyanine dyes, indigoid dyes, and mixtures thereof. The following is a generic structure for merocyanine dyes:

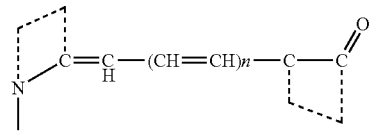

Solvatochromic dyes include the following dyes as illustrated below:

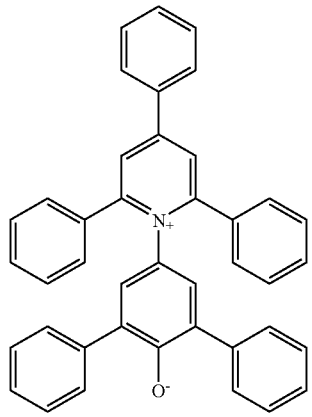

Reichard's Dye

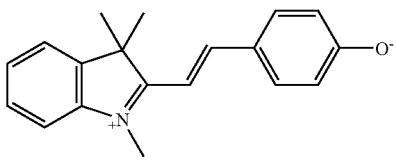

Merocyanine dye based upon Fischer's base.

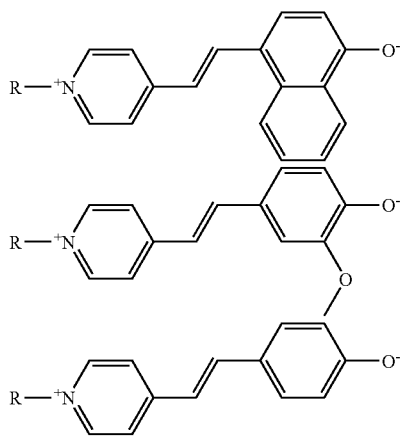

where R may be methyl, alkyl, aryl, phenyl.

The desired dye may be coated onto a substrate in any of the commonly used methods for coating substrates, such as dip and nip, spraying, ink jet printing, etc. The dye may also be physically adsorbed or covalently conjugated onto latex, silica or other polymeric particles, which may be placed on the substrate generally or in a pattern. This may be accomplished in a similar manner as the coating of toner particles onto a substrate in a photocopier or laser printer.

The amount of dye must be sufficient to allow a change in color upon contact with bacteria where the change is detectible to the unaided eye, and so will depend on the sensitivity of the dye. The amount of dye found to be sufficient is generally between 0.01 and 10 weight percent, more desirably between 0.05 and 5 and still more desirably between 0.1 and 3 weight percent on a dry basis. The color change occurs quite rapidly; in less than 1 minute, desirably in less than 30 seconds and most desirably in less than 20 seconds.

One way of practicing the instant invention is to incorporate a solvatochromic dye into a wipe, swab or dressing that may be rubbed against a surface upon which bacteria are suspected of being present. Such surfaces include, for example, railings, counter tops, cooking surfaces, foods like meat and fish and food packaging like films, the hands of children, food preparers, etc., bathroom surfaces, toys, babies skin, hospital surfaces, towels, sponges, dish towels, hospital garments and drapes, attachable stickers, electronic devices like telephones, keyboards, computer mice, utensils, wounds and cuts, door knobs, or any surface that may harbor bacteria.

Substrates onto which the solvatochromic dye may be coated may therefore include wipes, as well as other articles that may be exposed to bacteria like those mentioned above. The solvatochromic dyes may also be incorporated into lotions or cream used to check the hands for microbial contamination. The dye may be incorporated into sponges or dish towels to warn of contamination.

Substrates suitable for use as a wipe for coating with solvatochromic dyes include any of those traditionally used for wipes including films, woven and nonwoven fabrics, cellulosic substates like tissues, paper towels and coform materials, airlaid materials, bonded-carded webs and so forth. Nonexclusive examples of substrates may be found in U.S. Pat. Nos. 4,775,582 and 4,853,281, 4,833,003, and 4,511,488, all assigned to the Kimberly-Clark Corporation.

A nonwoven fabric may be made according to processes like spunbonding, meltblowing, airlaying, bonding and carding, and so forth. Nonwoven fabrics may be made from thermoplastic resins including, but not limited to polyesters, nylons, and polyolefins. Olefins include ethylene, propylene, butylenes, isoprene and so forth, as well as combinations thereof.

"Spunbonded fibers" are small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more desirably, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, natural polymers (for example, rayon or colton fibers or other cellulosic materials) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

A bonded carded web is made from staple fibers which are sent through a combing or carding unit, which breaks apart and aligns the staple fibers in the machine direction to form a generally machine direction-oriented fibrous nonwoven web. Once the web is formed, it then is bonded by one or more of several methods such as powder bonding, pattern bonding, through air bonding and ultrasonic bonding.

In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another. Examples of airlaid teachings include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

The inventors have discovered that bleaches used to clean surfaces like, for example, sodium hypochlorite solution, chlorine, and sodium bisulfite could possibly negatively impact solvatochromic dyes and cause a color change even though bacteria is not present. Another aspect of the invention, therefore, includes a bleach detector colorant in a wipe along with solvatochromic dyes. The indicator could be, for example, 2,2',5,5'-tetramethyl benzidine, which is normally colorless and turns red when exposed to chlorine or sodium hypochlorite. The indicator could also be a combination of starch and iodine which turns black in the presence of chlorine or hypochlorite. Yet another indicator, fuchsine, may be useful for detection of sulfites, such as sodium metabisulfite. Fuchsine is pink and changes to colorless when exposed to sulfites. In this way, areas of the wipe may be designated as sensitive to bacteria and other areas as sensitive to bleaches and preservatives so that surfaces containing active bleach give color change combinations that allow the user to distinguish bacteria contamination from bleach. The bleach indicator could be printed in a pattern to spell the word "BLEACH", hidden on the wipe so that if the wipe were passed through bleach, the word BLEACH would become visible, along with any other color change that the bleach may cause to the solvatochromic dye. The amount of bleach indicator need only be an amount sufficient to cause a color change that may be detected by the unaided eye and is in the same range as the solvatochromic dye.

The inventors also believe that it is possible to include small swatches of a) a solvatochromic dye that detects bacteria, b) a chlorine/hypochlorite detector material, such as tetramethyl benzidine, c) an oxidizing agent detector such as a mixture of starch and potassium iodide, d) a bisulfite indicator such as fuschine, e) a nitrite detecting reagent, as examples, onto an indicating strip. In this way, a variety of quality indicators could give a status or quality of, for example, food.

In another aspect of the invention, a coating on the substrate may be used to inhibit the solvatochromic dye from crystallizing, thereby obtaining a coating that has greater sensitivity to bacteria. Ideally, a coating that has single dye molecules on the surface would have greater sensitivity for bacteria. Each dye molecule would be free to interact with the bacteria membrane. In contrast, small crystals of dye first have to dissolve and then penetrate the membrane. While not wishing to be bound by theory, we believe that hydroxypropyl-beta-cyclodextrin, hydroxyethyl-beta-cyclodextrin, gama-cyclodextrin, hydroxypropyl-gama-cyclodextrin, hydroxyethyl-gama-cylodextrin (hereinafter collectively "cyclodextrin"), all available from Cerestar International of Hammond, Ind., USA, hinder the crystallization of the dye, allowing a more vivid dye color to occur on the substrate. The amount of cyclodextrin has been found to be effective is between 0.01 and 10 weight percent, desirably between 0.1 and 5 weight percent and still more desirably between 1 and 4 weight percent.

Another method of utilizing the solvatochromatic dyes to detect bacteria is in the form of a lateral flow detection device. Such devices 2, as shown in FIG. 1, have a deposition pad, membrane, and a wicking pad, (not visible separately) though in some embodiments the deposition pad may be optional. The device 2 has a detection zone 4 and a control zone 6. In use, a liquid sample is deposited on the device 2 in a sample area 8 and flows through the device 2 toward the wicking pad 10, passing through the detection zone 4. Sovatochromic dye is deposited in the detection zone 4, in a line in this case though other shapes could be used, and in the control zone 6, also in a line. As the sample moves through the detecton zone 4, if bacteria is present, the dye in the detection zone 4 will change color. The dye in the control zone 6 will not change color since the bacteria will be captured in the detection zone 4. The control zone 6 is used to indicate that the assay is running properly. The color of the detection zone 4 can be compared to the color of the control zone 6 to indicate the relative magnitude of the bacteria present. More than one solvatochromic dye line may be used since the sensitivity of dyes to different bacteria differs. Some dyes, for example, are more sensitive to gram positive bacteria and some are more sensitive to gram negative bacteria. In this way more than one type of bacteria may be detected.

The following examples aid in understanding the invention.

General Method Used to test Substrates with Dye Coating:

The dye coated sheets were tested for color change visible to the eye using the following microorganisms listed in USP (United States Pharmacopoeia) XXIV as opportunistic pathogens: *S. Aureus* (ATCC #6538), *E. Coli* (ATCC #8739) and *P. aeruginosa* (ATCC #9027). *Salonella* was also used.

Lyophilized cultures of the above listed organisms were started in 5 ml tubes of sterile trypticase soy broth (TSB) commercially available from Becton Dickinson (BBL) Labs. To maintain stock cultures at the same bacterial cell concentration day to day, one (1) drop (approx. 0.1 ml) was aseptically transferred from each stock culture to a new 5 ml tube of sterile TSB using a sterile transfer pipet. Five (5) culture transfers were made for each organism before any were used for sensitivity testing.

Starting with stock culture concentrations of $10^9$ to $10^8$ CFU (colony forming units)/ml, 1:10 serial dilutions were made using 9 ml volumes of sterile deionized water. Depending on the concentration desired, the following dilutions were typically made: $10^7$, $10^6$, $10^5$, $10^4$, and $10^3$ CFU/ml. Viable plate counts were performed on all stock cultures before sensitivity testing started. These counts along with the serial dilutions made, were used to calculate the actual bacterial concentrations for the testing performed.

The volume used to perform the sensitivity testing on all paper towels was 100 microliters. All testing was performed in a certified Laminar Flow (Class 100) Hood by a trained microbiologist. When testing was completed, all materials and bacterial cultures were exposed to a steam sterilization cycle (2500° F. & 18-22 PSI) for a period of 45 minutes.

EXAMPLE 1

The dye candidate (Reichart's Dye) was coated onto a Scott paper towel (0.5 g of dye in 20 ml of isopropanol), dried and tested by placing an aliquot (100 microliter) of liquid containing a known concentration of harmful bacteria.

The dye turned colorless in less than 10 seconds in the area wet by the bacteria containing spot, indicating the presence of bacteria. A similar sized spot of the media liquid, that did not contain bacteria, did not change color. Initially, a bacterial concentration of $10^8$ colony forming units per ml was spotted onto the coated towel. The bacteria suspensions were diluted with water to reduce the bacteria concentrations and a second drop was placed on the towel below the first drop. The experiments were repeated until the spot did not show a visible change.

The bacteria used in this test were *E. coli, P. aeruginosa, Salmonella* as viable gram negative bacteria, *Staphlococcus aureus*, and *S. xylosis* as viable gram positive bacteria, and *S. aureus* and *S. xylosis* as dead bacteria.

This testing method resulted in the visible detection of gram negative bacteria as low as 1000 colony forming units/milliliter (CFU/ml) and gram positive bacteria as low as 100 CFU/ml. The following table contains the results of testing of the bacteria at various concentrations. The results are the time in seconds for a color change to fully develop, (time in seconds vs. CFU/ml vs. bacteria type).

| Microbe Conc. in CFU/ml | E. Coli. | P. Aeruginosas | Salmonella | S. Xylosis | S. Aureus | S. Xylosis (Dead) | S. Aureus (Dead) |
|---|---|---|---|---|---|---|---|
| $10^8$ | <3 | <3 | <3 | <3 | <3 | <3 | <3 |
| $10^7$ | <3 | <3 | <3 | <3 | <3 | <3 | <3 |
| $10^6$ | <5 | <5 | <3 | <3 | <3 | <3 | <3 |
| $10^5$ | <5 | <5 | <5 | <3 | <3 | <5 | <5 |
| $10^4$ | <10 | <10 | <5 | <5 | <5 | <5 | <5 |
| $10^3$ | <10 | <10 | ND | <10 | <10 | <10 | <10 |
| $10^2$ | NC | NC | ND | <10 | <10 | <10 | <10 |

ND = Not determine, no experiment tried.
NC = No change in color.

In order to show that the dye had actually changed color, as opposed to being subjected to some sort of bleaching or destruction by the bacteria, a drop of isopropanol was placed in the same area of the towel that had previously been used to detect bacteria. The area wetted by isopropanol immediately turned blue, showing that the dye was still present on the towel and had not been washed away, metabolized or otherwise destroyed.

EXAMPLE 2

A solvatochromic dye, in this case merocyanine dye, (from Sigma-Aldrich Chemical) was coated onto a Scott® paper towel by the dip and dry method, in an amount of 0.5 g in 20 ml of water, and allowed dry. The dried paper towel was orange in color.

The solvatochromatically treated paper towel was tested by placing 100 microliters of human urine that had been aged at 25° C. for two weeks and had a bacterial concentration greater than 10,000 CFU/ml. The dye turned yellow in less than 5 seconds in the area wet by the bacteria, thus indicating the presence of the bacteria. A sample of urine was filtered with a 0.2 micron filter to remove microbial contamination and deposited on the treated towel and there was no color change. This indicates that there was no interference by any other agents or chemicals in the urine.

EXAMPLE 3

Millipore nitrocellulose HF75 membrane (from Millipore Corporation of Billerica, Mass., USA) was laminated onto a plastic supporting card (from Millipore Corp.) having a length of approximately 30 centimeters. On both the detection zone and control zone, a solution of 5 weight percent Reichardt's dye in iso-propanol was hand striped. The membrane was dried in a laboratory oven for 1 hour at a temperature of 37.5° C. After the membrane card was taken from the oven, a cellulosic wicking pad (Cat# CFSP203000 from Millipore Corp.) was attached to one end of the membrane closer to the control zone. The other end of the card, used to attach the sample pad, was cut off. The card was then sliced into 4 mm strips to form half sticks.

Once the half sticks were prepared, a bacteria solution was applied to the end of the detection membrane. Capillary action pulled the solution and bacteria into the detection zone and a color change was noted in the detection zone. The control line color remained the same through out the test.

EXAMPLE 4

A quantity of water may be tested for bacterial contamination. The inventors believe that 10 ml of the water, for example, may be tested by the addition of 1 microgram of solvatochromic dye. Alternatively, a wipe or piece of wipe as prepared in Examples 1 or 2 may be added to the water. It is believed that the color will change from the neat dye color to another color if there is sufficient bacteria present.

EXAMPLE 5

A Scott® paper towel was first coated with hydroxypropyl-beta-cyclodextrin (from Cerestar International, Hammond, Ind., USA) in solution in water (1 gram in 20 ml) by dipping and air-drying at ambient temperature. When dry the coated paper towel was treated with a solution of Reichardt's dye in isopropanol (1 weight percent) and allowed to air-dry. The dried towel was a purple/blue in color. Here the cyclodextrin hinders the crystallization of the dye allowing a more vivid color of the dye to occur on the paper towel. This coated towel was used in a test with gram-negative bacteria (*E. Coli*) and found to turn colorless in less than 5 seconds when an aliquot of 100 microliters of media containing 10,000 CFU/ml was applied to the towel. This decolorization was found to occur down to the bacteria concentration of 500 CFU/ml, though this took as long as 15 seconds. Thus by hindering the dye from crystallizing, the dye is believed to be present on the substrate as single molecules and therefore the sensitivity of the dye to bacteria levels increases. The inventors believe that by careful use of a coating (e.g. cyclodextrin) on the towel a mono-molecular coating of dye will occur on the surface of the substrate and maximum sensitivity will occur.

EXAMPLE 6

A test using the Reichardt's dye coated paper towel with a "dry" bacteria sample, not in solution was carried out. A dry sample of a colony of *E. Coli* bacteria lifted off an agar petri dish containing a series of growing cultures was used. This dry sample was then rubbed onto a pre-moistened dye coated Scott® paper towel. The area where the colony was placed and rubbed turned colorless within 1-5 seconds. This is a similar to how a wet wipe towel would be used and it performed well.

EXAMPLE 7

Bleach Indicator Test:

A mixture of Reichardt's Dye and 3,3',5,5'-tetramethylbenzidine (TMB) was coated onto a Scott® paper towel and allowed to air-dry. A dilute bleach solution was applied to the paper towel which resulted in the Reichardt's dye de-colorizing and the TMB turning orange/yellow color. This shows that a bleach indicator can be built into a bacteria indicating wiper.

In the final test, a Scott® paper towel having a coating of Reichardt's dye and TMB chemistries was exposed to suspension of *E. Coli* bacteria drop-wise. The towel area that came in contact with the bacteria decolorized to a white spot in less than 10 seconds. No orange/yellow color was observed to develop.

EXAMPLE 8

The potential interference or false positives that might occur when the dye coated substrate is used in the presence of soaps, detergents and alcohols was explored by depositing aliquots of the following solutions onto a dye coated towel and performing a visual examination for any color change.

SOAP—Kimberly-Clark Professional antibacterial Clear Skin Cleanser (PCSC C2001-1824) liquid soap.
   DETERGENT—AJAX® liquid dish detergent.
   ALCOHOLS—Ethanol and iso-propanol, Water solutions at a number of concentrations of each of the above did not give any color change.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A wipe configured to contact a surface on which bacteria are present, the wipe comprising a nonwoven web material on which is coated Reichardt's dye in an amount effective to undergo a detectable color change upon exposure to the bacteria, the nonwoven web material comprising cellulosic fibers.

2. The wipe of claim 1 wherein said dye is present in an amount of between about 0.01 and 10 weight percent on a dry basis.

3. The wipe of claim 1 further comprising a cyclodextrin selected from the group consisting of alpha-cyclodextrin, beta-cyclodextrin, gamma-cyclodextrin, hydroxyethyl-cyclodextrin, hydroxypropyl-cyclodextrin, and mixtures thereof.

4. The wipe of claim 3, wherein said cyclodextrin is present in an amount of between about 0.01 and 10 weight percent.

5. The wipe of claim 3 wherein said cyclodextrin is present in an amount between about 0.01 and 3 weight percent.

6. The wipe of claim 1 wherein the detectable color change occurs in less than 1 minute after exposure to bacteria.

7. The wipe of claim 1 wherein the detectable color change occurs in less than 30 seconds after exposure to bacteria.

8. The wipe of claim 1 wherein the detectable color change occurs in less than 20 seconds after exposure to bacteria.

9. The wipe of claim 1 further comprising a bleach detector colorant.

10. The wipe of claim 9 wherein said colorant is selected from the group consisting of 2,2',5,5'-tetramethyl benzidine, starch and iodine mixtures, fuchsine and mixtures thereof.

11. The wipe of claim 1, wherein the bacteria is gram negative bacteria.

12. The wipe of claim 1, wherein the bacteria is gram positive bacteria.

13. The wipe of claim 1, wherein said dye is present in an amount of between about 0.05 and 5 weight percent on a dry basis.

14. The wipe of claim 1, wherein said dye is present in an amount of between about 0.1 and 3 weight percent on a dry basis.

15. The wipe of claim 1, wherein the nonwoven web material further contains spunbonded fibers, meltblown fibers, or a combination thereof.

16. The wipe of claim 15, wherein the nonwoven web material contains a coform web.

17. The wipe of claim 1, wherein the nonwoven web material contains an airlaid web.

18. The wipe of claim 1, wherein the nonwoven web material contains a bonded carded web.

19. The wipe of claim 1, wherein the wipe is a tissue.

20. The wipe of claim 1, wherein the wipe is a paper towel.

* * * * *